United States Patent [19]

Avitall

[11] Patent Number: 5,263,493
[45] Date of Patent: Nov. 23, 1993

[54] DEFLECTABLE LOOP ELECTRODE ARRAY MAPPING AND ABLATION CATHETER FOR CARDIAC CHAMBERS

[76] Inventor: Boaz Avitall, 4868 N. Ardmore Ave., Milwaukee, Wis. 53217

[21] Appl. No.: 909,869

[22] Filed: Jul. 7, 1992

Related U.S. Application Data

[63] Continuation-in-part of Ser. No. 840,162, Feb. 24, 1992, abandoned.

[51] Int. Cl.[5] .............................................. A61N 1/05
[52] U.S. Cl. .................................... 607/122; 128/642
[58] Field of Search ............... 128/639, 642, 784–786, 128/790; 606/45, 46, 47, 48, 49

[56] References Cited

U.S. PATENT DOCUMENTS

| | | | |
|---|---|---|---|
| 4,522,212 | 6/1985 | Gelinas et al. | 128/786 X |
| 4,638,802 | 1/1987 | Okada | 606/47 |
| 4,641,649 | 2/1987 | Walinsky et al. | |
| 4,660,571 | 4/1987 | Hess et al. | |
| 4,677,990 | 7/1987 | Neubauer | 128/786 |
| 4,682,596 | 7/1987 | Bales et al. | |
| 4,699,147 | 10/1987 | Chilson et al. | 128/642 |
| 4,785,815 | 1/1988 | Cohen | |
| 4,869,248 | 9/1989 | Narula | 128/784 X |
| 4,882,777 | 11/1989 | Narula | 128/786 X |
| 4,920,980 | 5/1990 | Jackowski | 128/786 |
| 4,922,912 | 5/1990 | Watanabe | 128/786 X |
| 4,960,134 | 10/1990 | Webster, Jr. | 128/786 |
| 5,078,717 | 1/1992 | Parins et al. | 606/48 |
| 5,117,828 | 6/1992 | Metzger et al. | 128/784 |
| 5,156,151 | 10/1992 | Imran | 128/786 X |

*Primary Examiner*—William E. Kamm
*Assistant Examiner*—Samuel G. Gilbert
*Attorney, Agent, or Firm*—Haugen and Nikolai

[57] ABSTRACT

A cardiac arrhythmia mapping and ablation catheter has a main catheter that is provided with a mapping and ablation system attached to its distal end which includes an adjustable loop carrying an electrode array including a plurality of parallel-connected, separately operable mapping/ablation electrodes in conductive relation to the external environment and arranged in spaced serial relation along the loop. Insulated conductors connect the electrodes electrically with an input/output device outside the catheter for mapping the electrical activity of the chamber wall contacted and ablating tissue as indicated. Drawstring control wires are used to control the size, shape and deflection or posture of the loop. A distal extension may optionally be provided to adapt the loop specifically to addressing the tricuspid annulus. A fixed version is also disclosed.

24 Claims, 6 Drawing Sheets

DEFLECTABLE LOOP ELECTRODE ARRAY MAPPING AND ABLATION CATHETER FOR CARDIAC CHAMBERS

BACKGROUND OF THE INVENTION

I. Cross-Reference to Related Application

This patent application is a continuation-in-part of copending application Ser. No. 07/840,162, filed Feb. 24, 1992 now abandoned.

Reference is made to applications Ser. Nos. 07/835,553 and 07/840,026 of common inventorship. Both of these cross-referenced applications also are directed to improved catheters.

II. Field of the Invention

The present invention is directed generally to an improved catheter for us in the field of cardiac arrhythmia ablation. More particularly, the invention is directed to the use of a deflectable, preferably size and shape adjustable, electrode array loop catheter which allows the operator to rapidly map heart chambers and including the tricuspid annulus and ablate the desired tissue using the same mapping electrode in the array that is positioned on or near the site that should be ablated.

III. Discussion of the Related Art

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the A-V node in a slower fashion and continues to a common pathway known as the bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or injury which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is the more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This procedure involves extensive surgery in which an incision through the pericardium and heart muscle is made locate the arrhythmogenic tissue, which is then frozen or surgically removed to be replaced by scar tissue.

Because open-heart surgery is a high risk procedure which requires a prolonged period of hospitalization and recuperation, a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to the walls of the clogged vessel, thereby opening it.

Catheter devices have also been used to locate and ablate cardiac conduction pathways. One such device is shown in U.S. Pat. No. 4 785 815, in which a catheter tube carries at its distal end at least one electrode for sensing membrane potentials within the heart, together with a heating device for ablating at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4 869 248. These devices are generally effective once the ablating element is properly positioned at the localized area of interest. A catheter device of the class described has also been developed which employs a single handle operated deflection wire. Such a device is disclosed in U.S. Pat. No. 4 960 134.

Most present cardiac tissue ablation procedures involve the use of radio frequency (RF) electrical current transmitted to the tissue via a catheter which is positioned as closely as possible to the arrhythmogenic site within the atria or ventricles. Radio frequency electrical current heats the tissue surrounding the catheter, creating a discrete, dense lesion. In order for the patient to be cured of the arrhythmia, the lesion must be created in the area from which the arrhythmia originates. Improvement in the maneuverability of such devices and the accessibility of them to areas difficult to reach but which are common sources of abnormal rhythm would greatly assist optimization of arrhythmia location and precise positioning of the catheter prior to ablation.

In many patients with cardiac arrhythmias, the tissue that causes the abnormal rhythm is located in the right side upper chamber (atrium) at or near the tricuspid ring. The most appropriate location for ablation is defined by mapping a large area of tissue in order to identify the earliest electrical activity. The mapping process and the identification of the anatomical location of the catheter is at times a challenging and laborious procedure which as a result subjects the operator and patient to prolonged x-ray radiation.

Unlike with procedures for ablation of tissues around the mitral valve annulus, where a coronary sinus catheter readily provides crucial information as to the location of the arrhythmogenic tissue and also serves as a guide to the placement of the ablation catheter, no such structure is present at the right side of the heart around the tricuspid valve. A device which provided both the ability to rapidly map the entire tricuspid ring and areas adjacent to it, as well as the ability to apply the ablation energy to the most desirable location using the same catheter would not only expedite the ablation procedure, but also make it easier and more effective.

SUMMARY OF THE INVENTION

The present invention provides an unique mapping and ablation catheter device that provides both the ability to rapidly map cardiac chambers and also the entire tricuspid ring and areas adjacent to it, as well as the ability to apply the ablation energy to the most desirable location using the same catheter. This capability makes it easier to map the area of interest, and expedites and makes the ablation procedure more effective. The present invention is a new catheter design which incorporates a distal loop segment that can be opened and closed by tensing drawstring wires extending from the catheter handle. In one application, the loop is of a size designed to fit around the tricuspid valve. The most distal part of the loop may be provided with an extension in the form of a short length of flexible polyurethane tubing that can be inserted into the most anterior angle of the tricuspid ring. Without the extension, the device is suitable for mapping any other cardiac areas. While dimensions are not critical, the extension is normally about 4 French in diameter and less than an inch (18 mm) long. The loop extension provides an anchor for the loop at its distal end and the catheter shaft, from which the loop extends, is designed to be advanced into the inferior vena cava and provide the anchor for the loop at its proximal end.

The loop is equipped with a pair of arrays of serially distributed electrodes spaced apart and connected in a manner to allow recording from any location in the loop or around the tricuspid ring. In one arrangement, each electrode back side is shaved or flattened to permit the majority of the exposed surface to be in contact with the tissue and not with the blood. In one embodiment, the electrodes had a length of about 4 mm and were spaced about 2 mm apart. The system contains two deflection wires that are threaded in opposed relation along opposite sides of the loop arc extending thorough the loop and the main catheter lumen to the handle which control the size and shape of the loop. In this configuration, when these control wires are in their normal (untensioned) state, the loop remains closed with the opposite sides of the loop arc substantially parallel. Similar amounts of tension applied to both wires causes the loop to open symmetrically and remain in a constant position corresponding to the tensions applied; however, the pulling or tensing of but a single wire causes the loop to open asymmetrically and deflect toward the side of the loop arc opposite that being deflected. The loop is further mounted on a rigid sheath of strong thermoplastic material which is capable of sustaining the high pull forces on the deflection wires without damage, as well as maintaining a predetermined shape modified by heating the shaft and bending as required for the particular procedure. Once the thermoplastic catheter shaft is cooled, the angulation which was applied to the catheter during heating will be maintained. This construction enables the operator to rotate the catheter loop and control the location of the tip in a more positive manner.

The predetermined selected shape of the shaft allows the operator to advance the catheter loop sheath carrying the loop more readily into the tricuspid ring from the inferior vena cava. The configuration is such that rotation of the shaft causes the loop to rotate along the axis of the tricuspid ring, which allows the operator to map atrial and ventricular electrical activity at the posterior and anterior aspect of the tricuspid ring. The operator can readily change the catheter deflection by applying tension on one of the pull wires to change the loop angle with respect to the catheter shaft, thus providing greater flexibility of angles and shapes to accommodate the varying anatomical positions of the tricuspid ring.

BRIEF DESCRIPTION OF THE DRAWINGS

In the drawings, wherein like numerals are utilized to designate like parts throughout the same.

DETAILED DESCRIPTION

Figures 1A, 1B:
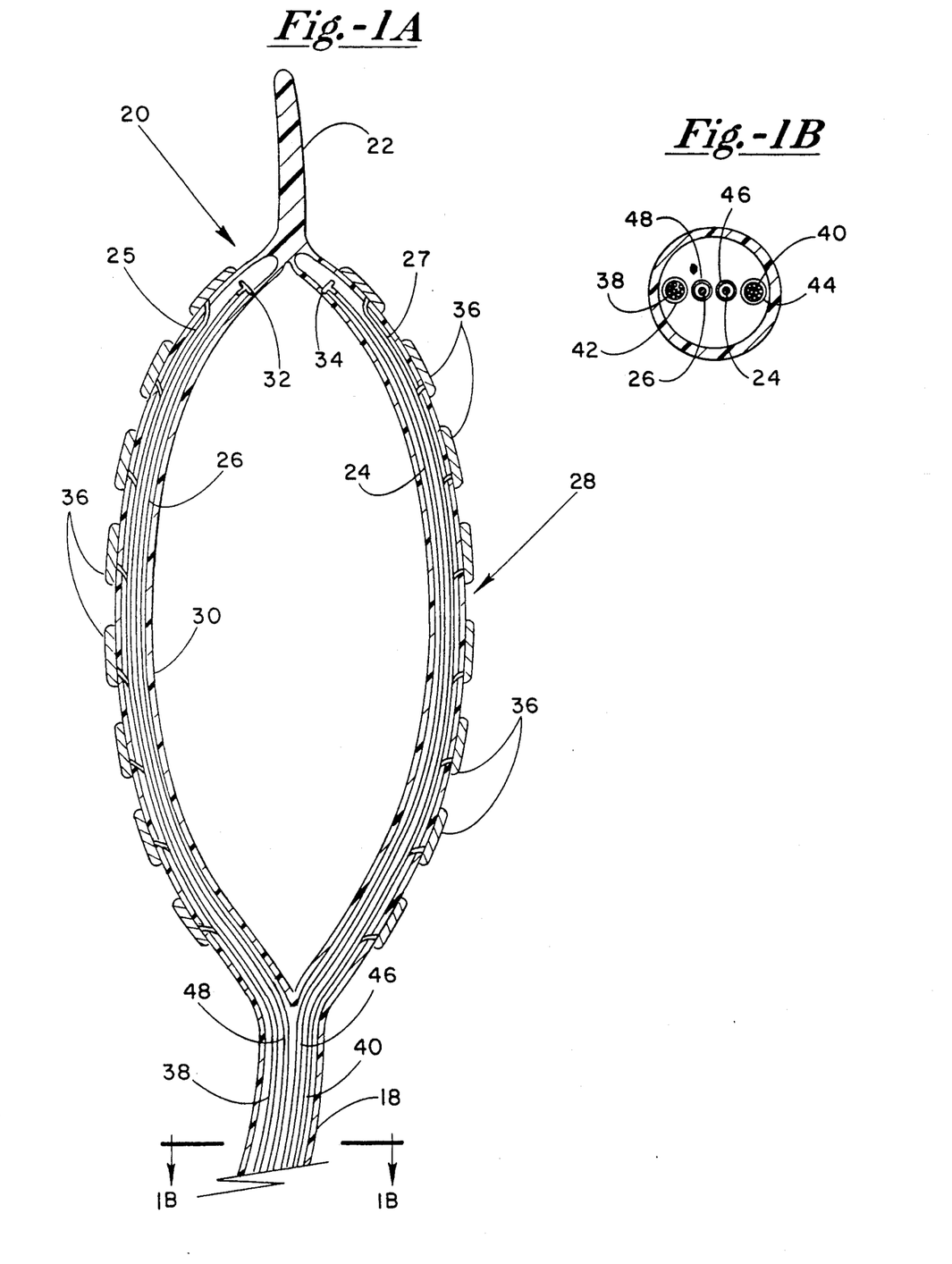
FIG. 1A is a greatly enlarged schematic view of the electrode array loop of the invention.
FIG. 1B is a cross-section view along lines 1B—1B of FIG. 1A.

The invention will next be described with reference to the several views of the drawings. The loop shown generally at 20 in the enlarged schematic view of FIG. 1A is made of thick but flexible reinforced polymer tubing (typically 1.7 mm in diameter) which is configured to form an ellipse when opened. The loop of polymer tubing, in this embodiment, is provided with a distal extension or appendage 22 also of a compatible polymeric material such as polyurethane. By way of example, the extension 22 may be 18 mm long by 4 French in diameter. The loop 20 also includes a pair of deflectio control wires 24 and 26 each anchored to the distal portion of the respective half of the tubular elliptical loops 28 and 30 by respective T-shaped pins 32 and 34.

The further contains a series of spaced tubular noble metal electrodes shown in part at 36 on either half of the elliptical loop which are further attached to individual respective insulated conductor wires as at 25 and 27 which may be bundled as represented by 38 and 40. Both the deflection control wires 24 and 26 and the conductors 38 and 40 are threaded through the respective loop lumen and the main catheter sheath to the control handle. The deflection control wires 24 and 26 thread through individual carrier tubes 46 and 48, respectively.

Figures 2A, 2B, 2C, 2D, 2E:
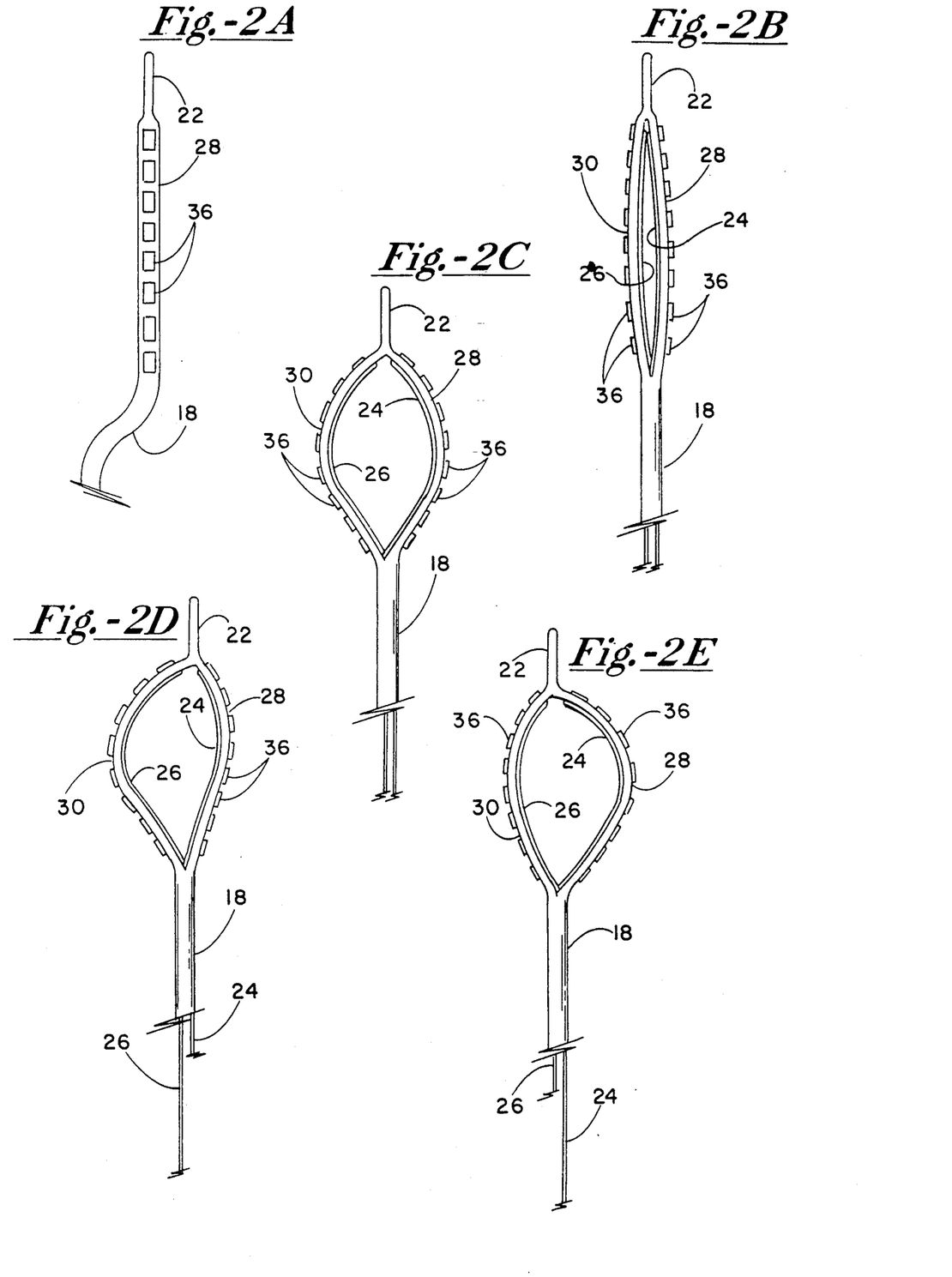
FIGS. 2A–2E are schematic views of the electrode array loop in a variety of dispositions and degrees of openness.

As better seen in FIG. 2A, when the loop is fully closed, it forms a substantially straight line. While dimensions are not critical, the length of the long axis is typically about 6 cm and the loop extension segment 22 about 18 mm. The electrodes 36 are preferably made of platinum tubing 2 mm thick and 4 mm long.

Figure 3A:
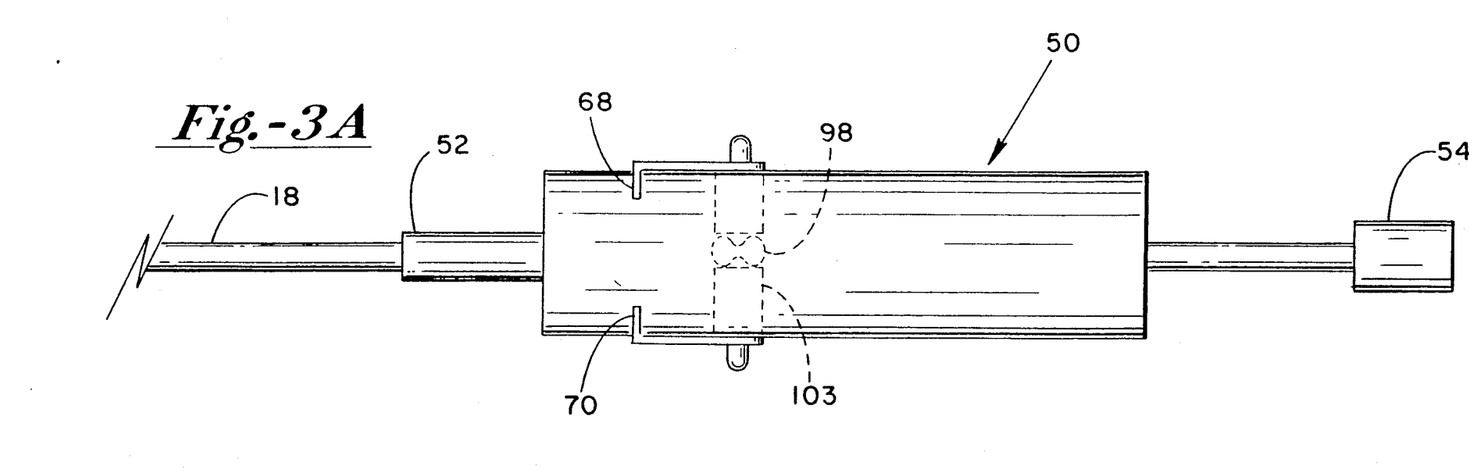
FIGS. 3A and 3B are schematic side and top views, broken, and partially in section, with parts cut away of a catheter and handle for use with the electrode array.
Figure 3B:
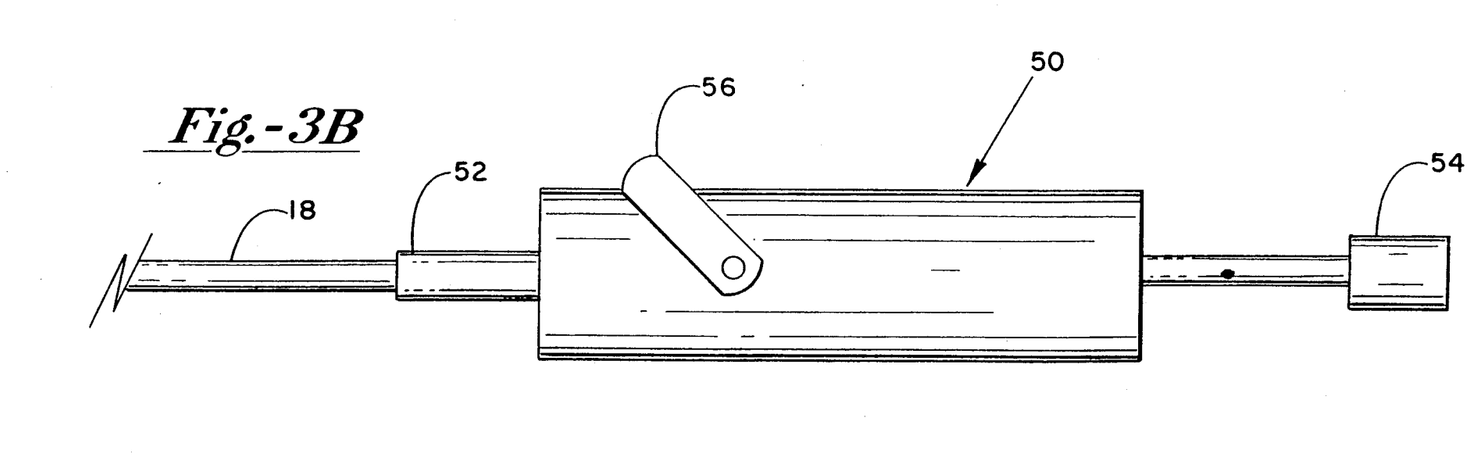

Prior to securing the electrodes, each of the platinum tubing segments 36 is attached to a respective low resistance conductor wire as at 25 and 27 nominally 0.08 mm in diameter that are threaded through small holes in the tubing (not shown). Each set of conductor wires 38, 40 is inserted into a polymer, preferably polytetrafluoroethylene (PTFE), tube as at 42, 44 that is disposed inside and extends the length of the main catheter shaft 18. This protects the conductor wires and carries them to an electrical connector which is mounted on a short cable on the proximal end of the catheter handle (FIGS. 3A and 3B).

Figure 6A:
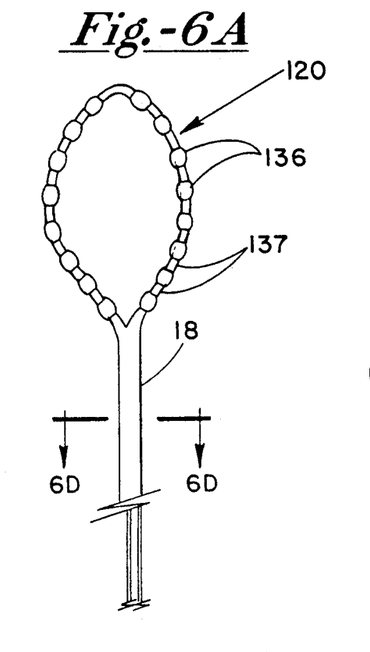
FIGS. 6A–6D are schematic views of the electrode array loop showing a variety of deflection dispositions.
Figure 6B:
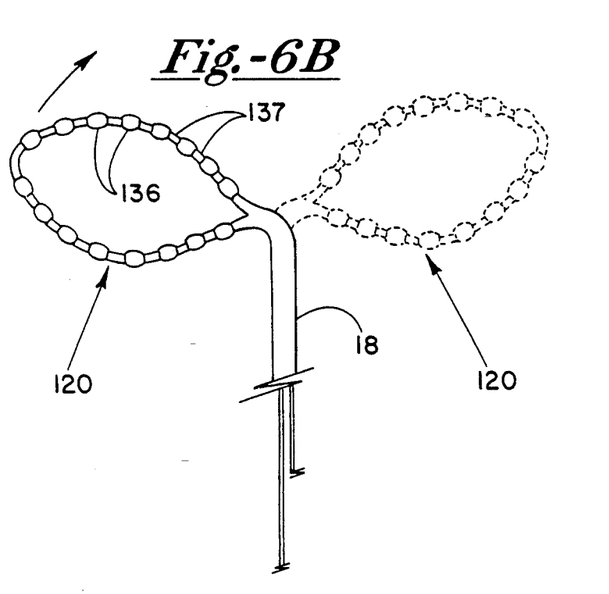
Figure 6C:
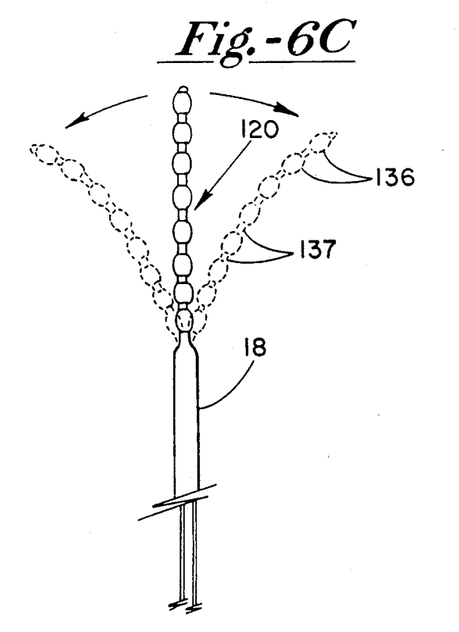

The tubular electrodes are also illustrated in FIGS. 6A-6C where a full view of the tubular segments is shown at 136. The electrodes 136 are likewise attached to individual respective insulated conductor wires shown bundled at 138 and 140 carried in tubes 142 and 144, respectively, in FIG. 6D. As with the electrodes 36, the electrodes 136 are typically 4-5 mm in length with any sharp edges removed and are separated by gaps 137 which may be any desired length but are typically about 2 mm. The control wire carrier tubes 146 and 148, respectively, carry control wires 124 and 126 as illustrated in the embodiment of FIGS. 1A and 1B. Control of individual electrodes for mapping activity and for ablation is the same as that of FIGS. 1A-1B and 2A-2E.

Regardless of electrode configuration, the main catheter shaft 18, then, contains four PTFE tubes, as shown in FIG. 1B, tube 42 carries the bundle of electrical conductor wires from the side 30 of the electrodes on the loop 20, 44 carries the bundle of electrical conductor wires from the side 28 of the electrodes on the loop 20. Tube 46 carries the pull wire 24 for the deflection of the lower loop segment 28 and 48 carries the pull wire 26 for the deflection of the loop segment 30. The deflection wires 24, 26 are preferably stainless steel, nominally 0.22 mm thick and attached to the T-shaped pins 32 and 34 (FIG. 1A) by crimping the respective pin onto the wire. The T-shaped pin and the pull wire are inserted into the loop tubing through a small hole in the inner aspect of the loop tubing. Each T-shaped pin may be imbedded into the tubing and secured with a compatible adhesive such as polyurethane glue.

As shown in FIGS. 2A-2E, when tension is applied to the deflection wires 24, 26, the upper and lower segments 28 and 30 will bend to form the loop which will result in the loop opening (2C). When the wire 26 is pulled alone or to a greater degree, the loop will open and deflect downward as shown in FIG. 2D. The reverse occurs when the lower wire 24 is pulled as illustrated in FIG. 2E.

Figure 6D:
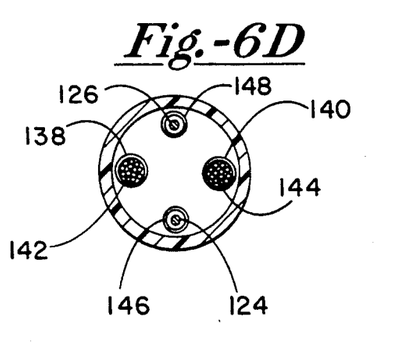

In FIG. 6D, control wires 124 and 126 are shown offset with respect to the conductor bundles 138 and 140 as opposed to the essentially in-line configuration of FIG. 1B, which is parallel to the plane of the undeflected electrode loop in its normal position parallel to the main catheter segment 18. The essentially 90° offset arrangement shown represents an exaggerated illustration pertaining to the use of the control wires for side-to-side deflection of the loop as shown in FIGS. 6B and 6C. Even with the in-line arrangement of FIGS. 1A and 1B, some side-to-side loop deflection control can be accomplished in addition to the loop shape control; and, it will be appreciated that any desired degree of offset, symmetrical or asymmetrical, can be employed.

Although dimensions are not critical, the distal portion of the main shaft 18 of the catheter is preferably about 8F in diameter and made of a reinforced thermosetting polymer tubing that can be reshaped by heating. The tubing is designed to be heated and shaped prior to use. Once cooled, the new shape is maintained with minimal deflection of the shaft even when high tension is applied to the loop deflection control or pull wires.

Figure 4:
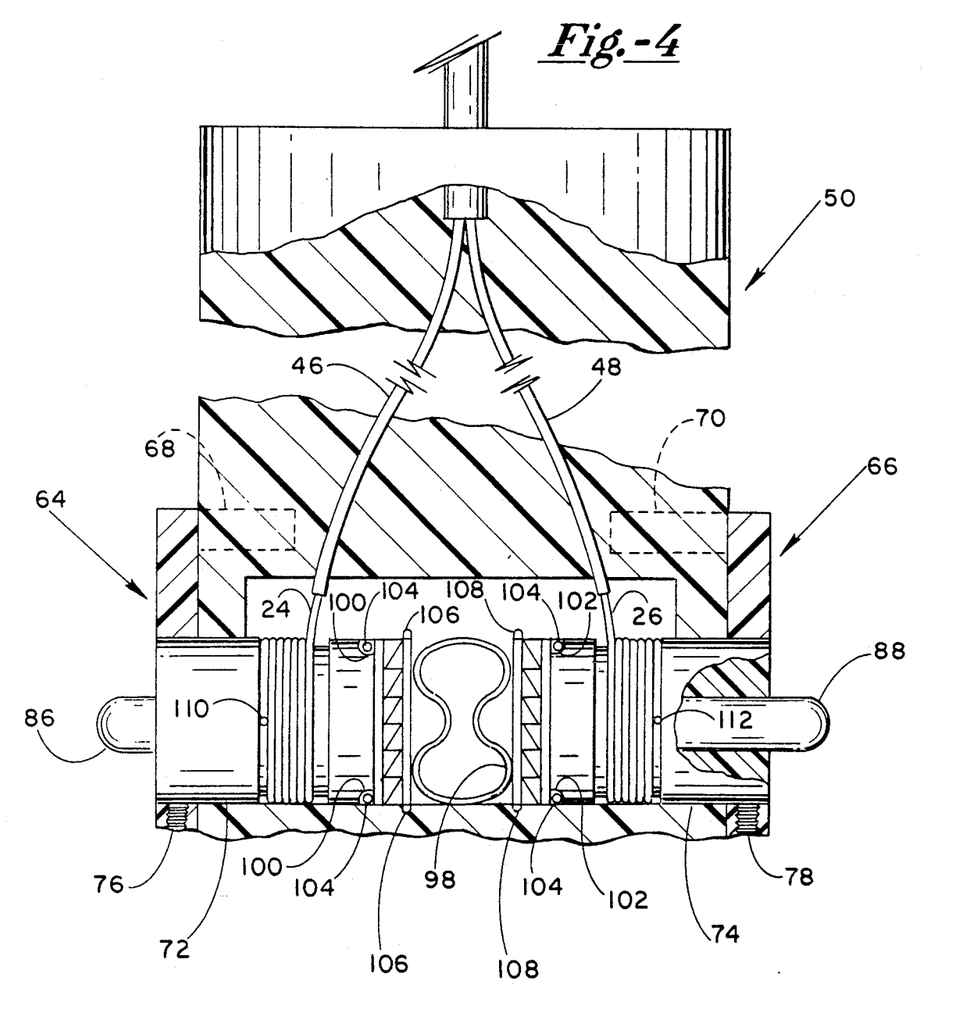
FIG. 4 is a schematic top view, broken, partially in section, with parts cut away of a catheter and handle for use with the electrode array.
Figure 5:
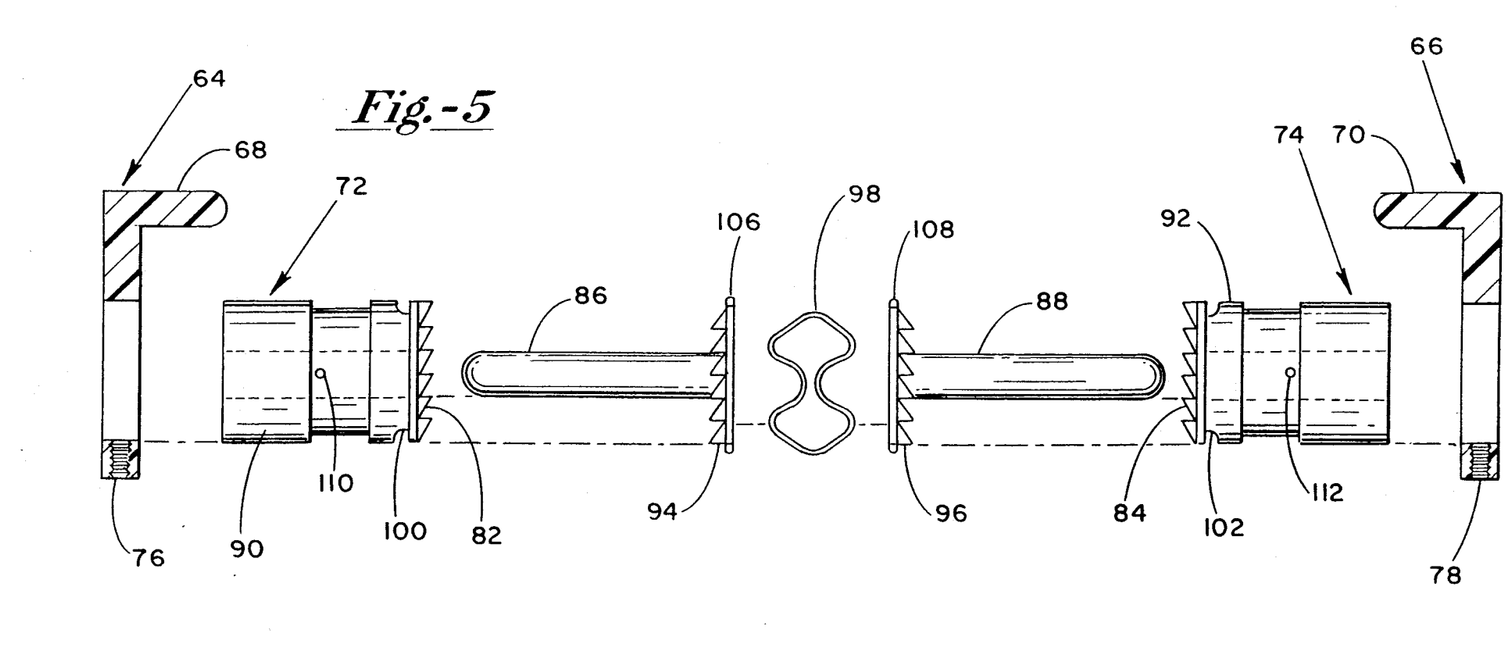
FIG. 5 is a greatly enlarged exploded plan view of parts of the handle of FIGS. 3A, 3B and 4.

The construction of the proximal end of and control handle elements for the catheter of the invention is illustrated in FIGS. 3-5. FIGS. 3A and 3B show the top and side view of the handle 50, generally. The catheter sheath 18 fits into the handle and the two bundles of electrical wires containing conductors connecting each electrode on the loop are threaded through the catheter tube segment 52 into and through the length of the handle to the proximal end of the handle 20 where they connect to a multi-pin input/output connector 54.

The two pull wires are attached to separate pull wire tension control systems and shown in greater detail in FIGS. 4 and 5. As seen in the exploded view of FIG. 5, the tension control systems and handle assembly include a pair of spaced symmetrical handle mechanisms. The tension control systems are shown in the form of opposite hand releasable ratchet mechanisms in which a pair of tension control lever members 64 and 66 with respective finger operated handle segments 68 and 70 are attached to hollow, generally cylindrical ratchet members 72 and 74 as by set screws 76 and 78. The ratchet members 72 and 74 have respective sets of unidirectionally engaging gear teeth 82 and 84 designed to cooperate with a resilient engaging and release mechanism which includes a pair of oppositely disposed locking members having shafts 86 and 88, designed to be journaled in bores 90 and 92 and having sets of gear teeth 94 and 96 disposed to mesh with respective teeth sets 82 and 84 as the locking members are urged outward by a spring member 98. As can best be seen in FIG. 5, the ratchet members 72 and 74 are provided with channels as at 100 and 102 which are designed to accommodate locking pins 104 when the tension control system is assembled in a handle bore 104 (FIG. 4).

As shown in FIG. 4, the loop deflection control wires 24 and 26 are threaded through openings 110 and 112 and attached to the ratchet members 72 and 74 and wound around them. Movement of the tension control lever handles 68 and 70 toward the proximal end of the handle draws the wires 24 and 26 and causes the loop to open. Each lever maintains its position upon release using the spring loaded gear tooth locking system which are caused to be continually engaged by the spring member 98. Rotation of the members 86 and 88 is prevented by two teeth 106 and 108, respectively, on each locking member that engage channels 103 (FIG. 4) in the handle member 50. Since each lever can be moved independently of the other, the deflection of the loop can be skewed or biased and thereby adjusted to better fit any shape of any chamber addressed. The tension on the deflection control wires is relieved individually by simply pushing in on the release knob ends of the members 86 and 88 to disengage the gear teeth and release the deflection control ratchet cylinder, allowing the corresponding handle to move back toward the closed loop position. To deflect or open the loop, the deflection control handle of interest can be moved without pressing the locking control knob, since the one-way locking teeth sets 82, 94 and 84, 96 slide on each other as a ratchet mechanism in one direction.

In operation, the catheter system is introduced by an incision into the vascular system of the patient and routed through the vascular system into the inferior vena cava such that the distal end of the main catheter extends into the right atrium chamber of the patient's heart. Once the proper position is reached, reciprocal movement of the handles 68 and 70 produces precise control of the size and shape of the loop 20 such that any point on the wall of the valve is readily accessible to the electrodes 36 of the ring 20. The distal tip of the catheter may also be extended through the tricuspid valve into the right ventricle to address the ventricular side of the tricuspid valve with the loop 20. The electrode members 36 can be utilized to map the cardiac depolarization potentials throughout the valve folds and surfaces, thereby locating and mapping any early activation sites. The tip extension is used to stabilize the loop location for mapping and for tissue ablation.

The ease and precision of the mapping made possible with the catheter system of the invention makes location of early activation sites and ablation of associated tissue with respect to the tricuspid valve area much easier and more precise. This makes the procedure much more practical than previous systems.

This invention has been described herein in considerable detail in order to comply with the Pat. No. Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself. For example, the loop can be made to conform to a fixed predetermined shape such as a fully open loop upon being deployed as it emerges from the catheter lumen. Memoried materials such as flexible but memoried plastics, or metallic materials such as a nickel titanium alloy commonly known as nitinol, can be employed in such an embodiment.

I claim:

1. A cardiac arrhythmia mapping and ablation catheter comprising:
    a main catheter comprising an elongated, flexible plastic tube having a proximal end and a distal end, and an outside diameter small enough to pass through a vascular systems from an introducer site into a desired cardiac chamber and having the capability required to negotiate the vascular system, the main catheter further describing a main internal lumen extending from the proximal end to the distal end;
    a mapping and ablation system attached to the distal end of the tube of the main catheter and further including,
        a distal adjustable tublar loop having generally oppositely disposed sections and carrying an electrode array including a plurality of externally conductive, individually connected mapping/ablation electrodes arranged in spaced serial relation along the adjustable tubular loop,
        insulated conductor means connecting the individual electrodes electrically with an input/output device outside the catheter for mapping electrical activity of a chamber wall contacted and ablating tissue as indicated,
        loop control means for adjusting and controlling shape and posture or deflection of the adjustable array loop comprising a pair of tension control members, each associated with a section of the adjustable tubular distal loop to apply a desired amount of tension or provide slack.

2. The cardiac arrhythmia ablation catheter of claim 1 wherein the pair of tension control members comprises a pair of tensioning drawstring wires.

3. The cardiac arrhythmia ablation catheter of claim 1 wherein the loop control means further comprises means for separately controlling the tension applied by each tension control member.

4. The cardiac arrhythmia ablation catheter of claim 1 wherein the tension control members are at least slightly offset with respect to a plane parallel to a plane described by the electrode array loop in an undeflected state to increase leverage relative to side-to-side deflection control of the loop itself.

5. The cardiac arrhythmia ablation catheter of claim 1 wherein the pair of tension control members are symmetrically placed with respect to controlling the shape and posture of the adjustable array loop such that each addresses a section of equal length in the loop.

6. The cardiac arrhythmia ablation catheter of claim 1 wherein the main catheter further comprises:
    control handle means for controlling the mapping and ablation system connected to the proximal end of the main catheter;
    a pair of tension control means in the catheter handle means, each one of the pair of tension control means being associated with a corresponding one of the pair of tension control members, for separately controlling tension in the corresponding one of the pair of tension control members; and
    wherein the pair of tension control members are threaded in opposed relation along opposite sides of the loop and extend through the loop and the main catheter lumen and including means separately connecting each tension control member to a corresponding tension control means, each tension control member thereby controlling tension in the respective connected side of the loop.

7. The cardiac arrhythmia ablation catheter of claim 6 wherein each one of the pair of tension control means further comprises hand-operable releasable ratchet mechanism having tension control lever member attached to rotate a generally cylindrical adjustable tension controlling ratchet member to which the corresponding tension control means is fixed thereby causing the corresponding tension control means to wind and unwind and accordingly to apply tension to and relax an affected portion of the loop.

8. The cardiac arrhythmia ablation catheter of claim 7 wherein the tension control means further comprise resilient release means for individually disengaging each ratchet member to thereby release tension on a corresponding tension control member.

9. The cardiac arrhythmia ablation catheter of claim 6 wherein the pair of tension control members are symmetrically placed with respect to controlling shape and posture of the adjustable array loop such that each addresses a section of equal length in the loop.

10. The cardiac arrhythmia ablation catheter of claim 9 wherein the loop has a distal extremity and further comprises a length of flexible tubing extending from the distal extremity of the loop to aid in positioning the loop as for use at a tricuspid valve.

11. The cardiac arrhythmic ablation catheter of claim 10 wherein the length of flexible tubing is an extension of the loop.

12. The cardiac arrhythmia ablation catheter of claim 1 wherein the electrodes of the electrode array are raised and have exposed outer surfaces directed away from the loop which are substantially flattened to present a larger electrode contact surface to tissue contacted which is situated generally perpendicular to a plane described by the loop.

13. The cardiac arrhythmia ablation catheter of claim 1 wherein the electrodes of the electrode array are substantially tubular.

14. The cardiac arrhythmia ablation catheter of claim 1 wherein the elongated tube of the main catheter has a tube wall that is further characterized by having a segment thereof extending to the distal end, having a thermoplastic nature providing the ability to be heated and formed in a shape as desired, such formed shape being retained upon cooling.

15. The cardiac arrhythmia ablation catheter of claim 1 wherein the loop has a distal extremity and further comprises a length of flexible tubing extending the distal extremity of the loop to aid in positioning the loop as for use at a tricuspid valve.

16. A cardiac arrhythmia ablation catheter comprising:
   a main catheter comprising an elongated, flexible plastic tube having a proximal end and a distal end, and an outside diameter small enough to pass through a vascular system from an introducer site into a desired cardiac chamber, the main catheter further describing a main lumen extending from the proximal end to the distal end, the main catheter having the capability required to enable routing through the vascular system;
   a mapping and ablation system attached to the distal end of the tube of the main catheter and further comprising,
   an adjustable tubular distal electrode array loop having generally oppositely disposed sides configured to address a tricuspid annulus carrying an electrode array including a plurality of externally conductive, individually connected mapping/ablation electrodes arranged in serial spaced relation along the adjustable tubular loop,
   insulated conductor means connecting the electrodes electrically with one input/output device outside the catheter for mapping electrical activity of a chamber wall contacted and ablating tissue as indicated,
   a pair of tensioning drawstring wires for adjusting and controlling shape and posture of the adjustable array loop;
   control handle means for controlling the mapping and ablation system connected to the proximal end of the main catheter;
   a pair of tension control means in the control handle means for separately controlling tension in each drawstring wire of the pair; and
   wherein the pair of drawstring wires are threaded in opposed relation along the oppositely disposed sides of the loop and extend through the loop and the main catheter lumen and are each connected separately to a respective one of the pair of tension control means.

17. The cardiac arrhythmia ablation catheter of claim 16 further comprising a short length of flexible tubing extending the distal end of the loop to aid in positioning the loop for use at a tricuspid valve.

18. The cardiac arrhythmia ablation catheter of claim 16 wherein the tensioning drawstring wires are at least slightly offset with respect to a plane parallel to a plane described by the electrode array loop in an undeflected state to increase relative side-to-side deflection control of the loop itself.

19. The cardiac arrhythmia ablation catheter of claim 16 wherein the pair of tensioning drawstring wires are symmetrically placed with respect to controlling shape and posture of the adjustable array loop such that each addresses an equal section of the loop.

20. The cardiac arrhythmia ablation catheter of claim 16 wherein the electrodes of the electrode array are raised and have exposed outer surfaces directed away from the loop which are substantially flattened to present a larger electrode contact surface to tissue contacted which is situated generally perpendicular to a plane described by the loop.

21. The cardiac arrhythmia ablation catheter of claim 16 wherein the electrodes of the electrode array are substantially tubular.

22. A method of mapping and ablating tissue in a cardiac chamber of interest comprising the steps of:
   introducing a cardiac mapping and ablation catheter system into a vascular system at an introducer site, the catheter system having,
   a main catheter comprising an elongated, flexible plastic tube having aproximal end and a distal end, and an outside diameter small enough to pass through the vascular system from an introducer site into a cardiac chamber of interest and having the capability required to enable routing of the main catheter through the vascular system, the main catheter further describing main internal lumen of a relatively large size extending from the proximal end to the distal end;
   a mapping and ablation catheter system attached to the distal end of the main catheter and further comprising,
   an adjustable tubular distal loop having generally oppositely disposed sides carrying an electrode array including a plurality of externally conductive, individually connected mapping/ablation electrodes arranged in spaced relation along the adjustable distal loop,
   insulated conductor means connecting each electrode electrically with an input/output device outside the catheter for mapping electrical activity of a chamber wall contacted and ablating tissue as indicated, and control means for adjusting and controlling shape and posture or deflection of the adjustable array loop comprising a pair of tension control members each associated with a side of the adjustable tubular distal loop to apply an amount of tension or slack thereto as desired;

navigating the main catheter system along in a vascular system from an introducer site to access a heart chamber of interest and inserting the mapping and ablation catheter system into the chamber of interest;

using the pair of tension control members, each connected to one of the pair of tension control members to adjust an associated side of the adjustable tubular distal loop and loop deflection to conform to a shape of inner wall in the chamber of interest as required and using the electrodes to map electrical activity thereof;

using the electrodes of the tubular loop to ablate sites of early activity as required.

23. The method of claim 22 wherein the mapping and ablation catheter system further comprises:

a thermoplastic distal segment in the main catheter connecting the adjustable tubular distal loop; and wherein the method further comprises the step of using heat to shape the thermoplastic distal segment of the main catheter as required to allow the loop to address an interior wall in the chamber of interest.

24. The method of claim 22 wherein the adjustable distal tubular loop has a distal extremity; and wherein the mapping and ablation catheter system further comprises a short tubular extension of a distal extremity of the loop to aid in positioning the loop for use at a tricuspid valve; and wherein the method further comprises the step of:

inserting the tubular extension into a most anterior angle of a tricuspid ring; and using the control means to adjust the posture and shape of the loop to conform to an inner wall and map and ablate as needed.

* * * * *

UNITED STATES PATENT AND TRADEMARK OFFICE
CERTIFICATE OF CORRECTION

PATENT NO.   : 5,263,493
DATED        : November 23, 1993
INVENTOR(S)  : Boaz Avitall It is certified that error appears in the above-indentified patent and that said Letters Patent is hereby corrected as shown below:

In column 7, line 63, delete "systems" and insert -- system -- .

In column 8, line 36, delete "the".

In column 9, lines 55-66, and column 10, lines 1-3, should be double indented.

In column 10, line 47, delete "aproximal" and insert -- a proximal -- .

Signed and Sealed this

Seventeenth Day of May, 1994

Attest:

BRUCE LEHMAN

Attesting Officer   Commissioner of Patents and Trademarks